(12) United States Patent
Villar et al.

(10) Patent No.: US 7,585,529 B2
(45) Date of Patent: Sep. 8, 2009

(54) PROCESS TO EXTRACT GLUTEN FROM FOOD PRODUCTS AND KIT FOR ACHIEVING SAME

(75) Inventors: Elena Lopez Villar, Madrid (ES); Mercedes Llorente Gomez, Madrid (ES); Enrique Mendez Corman, Madrid (ES)

(73) Assignee: Consejo Superior De Investigaciones Cientitificas (ES)

( * ) Notice: Subject to any disclaimer, the term of this patent is extended or adjusted under 35 U.S.C. 154(b) by 793 days.

(21) Appl. No.: 10/477,935

(22) PCT Filed: May 3, 2002

(86) PCT No.: PCT/ES02/00208

§ 371 (c)(1),
(2), (4) Date: Mar. 9, 2004

(87) PCT Pub. No.: WO02/092633

PCT Pub. Date: Nov. 21, 2002

(65) Prior Publication Data

US 2004/0137137 A1 Jul. 15, 2004

(30) Foreign Application Priority Data

May 14, 2001 (ES) .............................. 200101098

(51) Int. Cl.
*C07K 16/16* (2006.01)

(52) U.S. Cl. .................... 426/425; 426/429; 426/656
(58) Field of Classification Search ................ 426/656, 426/429, 425
See application file for complete search history.

(56) References Cited

U.S. PATENT DOCUMENTS

RE32,919 E * 5/1989 Sarnoff .......................... 514/2
5,177,024 A * 1/1993 Chan et al. ................... 436/536

FOREIGN PATENT DOCUMENTS

GB 2207921 2/1989

OTHER PUBLICATIONS

Ellis et al. GUT. 1998. vol. 43, pp. 190-195.*
Peter J. Frazier, et al., "Lipip-protein Unteraction During Dough Development", J. Sci. Food Agric., 1981, vol. 32, pp. 877-897.
Aris Graveland, et al., "Extraction and Fraction of Wheat Flour Proteins", J. Sci. Food Argic., 1982, vol. 33, pp. 1117-1128.

* cited by examiner

*Primary Examiner*—Anthony Weier
(74) *Attorney, Agent, or Firm*—Ostrolenk Faber LLP

(57) ABSTRACT

The invention relates to a method for extracting the gluten contained in a sample using an ethanol aqueous solution in the presence of a composition containing a disulphur group reducer and a decoupling agent, in a buffer having a pH of between 7 and 8. The inventive method can be used to extract quantitatively the gluten contained in a heat-processed or non-heat processed food sample before the quantification of the gluten by ELISA. The method is suitable for food analyses, in particular, for foodstuffs intended for celiac sufferers.

19 Claims, 1 Drawing Sheet

PROCESS TO EXTRACT GLUTEN FROM FOOD PRODUCTS AND KIT FOR ACHIEVING SAME

CROSS REFERENCE TO RELATED APPLICATION

The present application is a U.S.C. § 371 national phase conversion of PCT/ES02/00208 filed May 3, 2002, which claims priority of Spanish Application No. P 200101098 filed May. 14, 2001.

AREA OF THE INVENTION

This invention, in general, refers to the analysis of food items for celiac patients and, especially, to a procedure to extract gluten from food products, compatible with an enzyme linked immunoabsorption assay (ELISA), to compositions suitable for the practical application of this procedure, to kits containing these compositions and to a method to quantify the gluten in the food products by ELISA.

BACKGROUND OF THE INVENTION

Celiac disease (CD) is a disease characterised by intolerance to the gluten prolamines of wheat, barley, rye and oats that causes intestinal alterations leading to malabsorption.

Gluten is a complex mixture of proteins and, although the toxic component or components responsible for CD are unknown, the temporary solution consists in eliminating all the gluten components from diets of these patients. In fact, the only truly effective treatment of celiac disease is to follow a strict gluten-free diet. It is, therefore, essential to be able to precisely quantify the amount of gluten in food items to be taken by celiac patients.

However, a reliable method to measure the gluten content of food items has been notably lacking over the last few years. At present, gluten is measured by epitope-dependent methods, such as ELISA, which use monoclonal or polyclonal antibodies. A useful ELISA technique to quantify the gluten contents of food products is described in Sorell et al., in the article titled "*An innovative sandwich ELISA system based on an antibody cocktail for gluten analysis*" published in FEBS letters, 439, 46-50 (1988).

The routine protocol for gluten analysis in food products, both for heat-treated and non heat-treated items, consists in extracting gluten with a 60% aqueous solution of ethanol (60% ethanol/water) followed by quantification by ELISA.

One of the main problems related with gluten analysis in food products lies in the fact that a large proportion of food products for celiac patients are processed at high temperatures (150-220° C.). Owing to this thermal treatment, most toxic glucose fractions ($\alpha$-, $\beta$-, and $\gamma$-gliadines) are denatured and made insoluble and can, therefore, not be extracted using 60% ethanol/water.

Consequently, the gluten measurement of these heat processed food products, regardless of the ELISA test used, is not reliable.

SUMMARY OF THE INVENTION

The invention faces the challenge of developing a process to quantitatively extract the gluten content of food items, which is compatible with ELISA, the technique currently used to quantify the gluten contents of food products.

The solution provided by this invention is based on the inventors' observation that the use of a composition comprised of a disulphide group reducing agent, a dissociating agent in phosphate buffer with a pH between 7 and 8, before extracting gluten with an aqueous ethanol solution of 60%, dissolves the toxic gluten fractions, permitting the gluten contents of the food products to be analysed quantitatively.

The yield of gluten extraction from food products reached by the process developed by this invention is much higher than that obtained by the conventional gluten extraction system based only on the use of 60% ethanol/water, such as that shown in Tables 1 and 2 (see Examples 1 and 3). Similarly, the recovery of gluten both from heat-treated and from non heat-treated food items is practically quantitative, as shown in FIG. 1 (see Example 2).

An object of this invention is a process to extract gluten from food products that is compatible with ELISA, that consists in extracting the gluten with an aqueous solution of ethanol in the presence of a composition containing a reducing agent of disulphide groups and a dissociating agent in a buffer with a pH between 7 and 8.

An additional object of this invention is a method to quantify by ELISA the gluten present in a food sample that consists in the previous extraction of the gluten contents of the sample by the above-mentioned gluten extraction process.

Another additional object of this invention is a kit that contains this composition to be used for the practical application of this gluten extraction process from food products, or its components separately. This kit can be used to extract the gluten contents in a food item as a previous step to quantification by ELISA of the gluten contents of a food item.

DETAILED DESCRIPTION OF THE INVENTION

Figure 1:
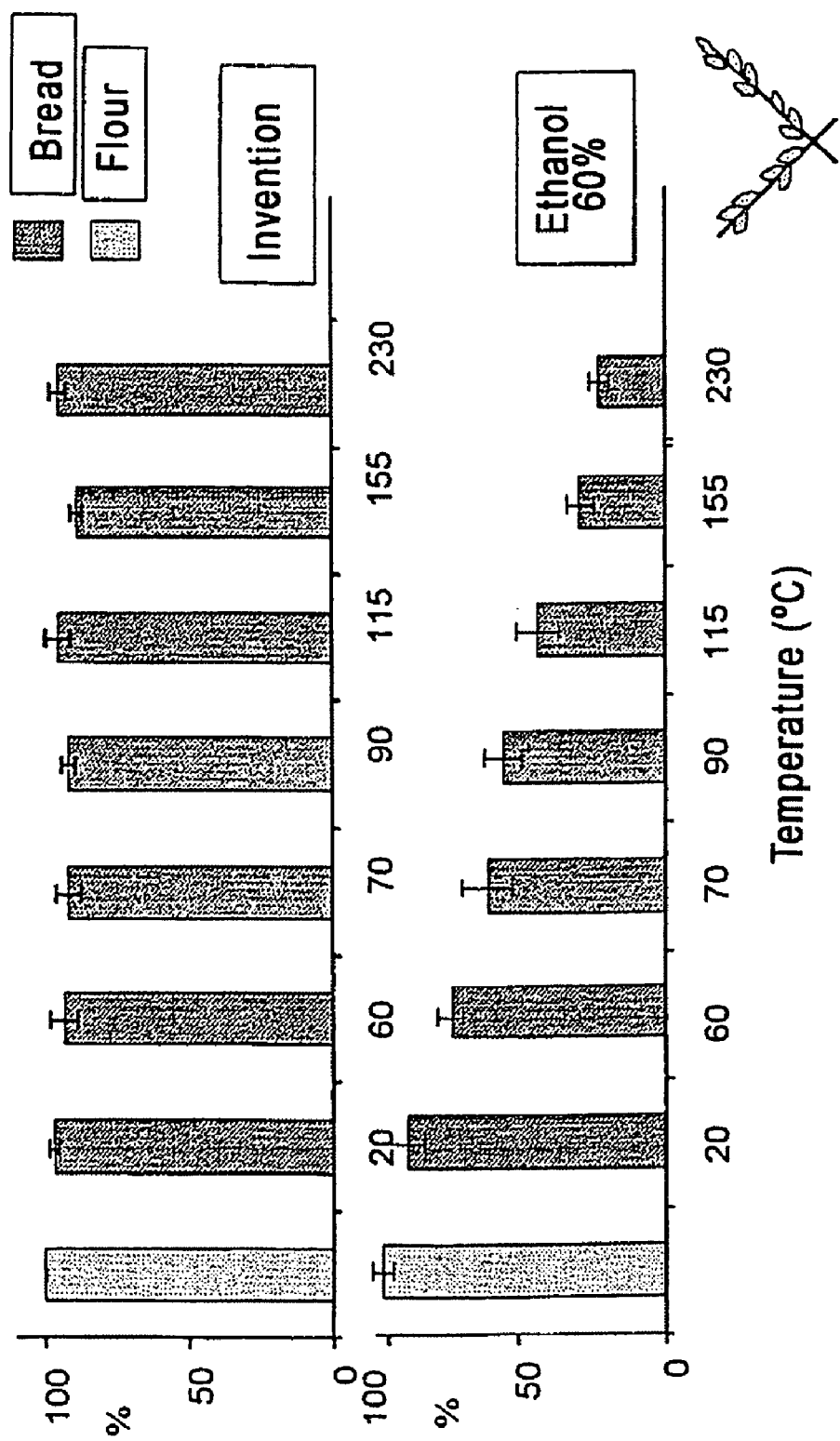
FIG. 1 is a bar chart that represents the percentage recovery of gluten in breads processed at different temperatures and also in the flour used to make these breads, extracted using the gluten extraction process provided by this invention (INVENTION) or by a reference method (60% ETHANOL) (see Example 2).

The invention provides a composition, from hereon referred to as the composition of the invention, that consists in a disulphide group reducing agent and a dissociating agent, in a buffer solution with a pH between 7 and 8.

The disulphide group reducing agent can be any compound capable of reducing disulphide groups such as, 2-mercaptoethanol (2-ME), dithiotreitol, etc. and mixtures of these. The concentration of the reducing agent of disulphide groups in the composition of the invention can vary within a wide range depending, among other factors, on the reducing agents of the disulphide groups in question.

The dissociating agent can be any compound with the ability to open the protein conformation making specific regions of the polypeptide chain more accessible to external reagents and antibodies, for example, guanidine hydrochloride, urea etc. and mixtures of these. The concentration of the dissociating agent in the composition of the invention can vary within a wide interval depending, among other factors, on the dissociating agent in question. In one application, the dissociating agent is guanidine hydrochloride and the concentration of this compound of the invention lies between 1 and 6M. Parallely, in another application, the dissociating agent is urea and the concentration of this compound in the composition of the invention lies between 1 and 5 M.

The buffer can be any pH regulator solution that buffers at a pH value between 7 and 8, such as, a phosphate saline solution (PBS) with a pH between 7 and 8, Tris with a pH between 7 and 8 etc.

In one specific application of the composition of the invention, the disulphide group reducing agent is 2-ME, the dissociating agent is guanidine hydrochloride and the buffer is PBS with a pH between 7 and 8.

The composition of the invention is useful as a "cocktail" to extract gluten from food items, both from heat-processed and non heat-processed products. It was also surprising to demonstrate that use of the compound of the invention for gluten extraction (that contains a disulphide group reducing agent and a dissociating agent with a phosphate buffer with a specific pH) does not adversely affect ELISA quantification of the gluten contents of a food item.

The invention also provides a process to extract gluten from a food sample, from hereon called the process of the invention, that consists in extracting the gluten contents from this sample with an aqueous solution of ethanol in the presence of the composition of the invention.

More specifically, the process of the invention, that consists in extracting gluten with an aqueous solution of ethanol and separating the supernatant that contains the extracted gluten, is characterised because before the extraction with this aqueous ethanol solution, the sample to be tested is mixed with the composition of the invention, incubated to a temperature between 37° C. and 50° C., for a period of time between 30 and 60 minutes and cooled to room temperature.

The ethanol concentration in the aqueous ethanol solution can vary within a wide interval. In one specific application this aqueous ethanol solution has an ethanol concentration of between 50 and 70%.

The food sample to be tested is prepared by conventional methods including, where relevant, grinding the sample and placing it in an appropriate recipient such as a propylene tube. Then, the composition of the invention is added, the recipient is closed and the resulting mixture is stirred. Preferably, the recipient containing the mixture is sealed, for example with parafilm, to avoid evaporation of this mixture by heat. In one specific application, incubation of the sample with the compound of the invention is done at a temperature of 50° C. for 40 minutes. After the incubation, the resulting mixture is left to cool to room temperature (between 15 and 25° C.). Then, an aqueous ethanol solution is added, such as a 60% aqueous ethanol solution, to this mixture and incubated to room temperature for an appropriate period of time, for example, at room temperature for 1 hour while stirring. After, the reaction mixture is centrifuged, the supernatant is removed (containing the extracted gluten) and, finally, the gluten contents are quantified by an ELISA technique of the type usually used to quantify gluten in food.

Using the procedure of the invention, almost the entire toxic fraction of the gluten contents of the heat-treated or not heat-treated food item, are dissolved. Although we do not want to associate the composition of the invention with any specific theory, the composition of the invention is thought to act by opening the conformation of proteins constituting the gluten, especially, its toxic fraction, and, consequently, to favour its solubility in the extraction medium. Indeed, during the heat treatment of food products, the gluten fractions (α-, β-, and γ-gliadines) are denatured, the disulphide bridges break and, consequently, insoluble aggregates form that cannot be extracted with 60% ethanol/water. Owing to the combined effect of the components of the composition of the invention i) the insoluble aggregate can be extracted with an aqueous ethanol solution (50-70/ethanol/water) and quantified by ELISA and (ii) the conformation of the gluten molecules increases leaving the antigenic determinants more exposed to the antibodies, causing the ELISA signal to increase.

Quantitative gluten extraction processes for food items compatible with ELISA used for gluten quantification are not known. It was surprising that the use of a disulphide bridge reducing agent, such as 2-ME, combined with a dissociating agent, such as guanidine hydrochloride, permits the gluten content of heat treated and non heat-treated food items to be extracted quantitatively (see Example 2) without adversely affecting their quantification by ELISA.

The results shown in FIG. 1 (Example 2) clearly indicate that the procedure of the invention is a very suitable tool to use before ELISA quantification of the food gluten contents for celiac patients in heat-treated and non heat-treated foods.

The process of the invention appears to consist, therefore, of a general extraction process for gluten from heat-treated and non heat-treated food products, especially developed for celiac patients, that dissolves the toxic fractions of gluten permitting the gluten in this type of food product to be analyzed quantitatively.

The invention also provides a method to quantify by ELISA the gluten present in a food sample that consists in extracting the gluten contents from this sample using the process of the invention and then, to quantify by ELISA the previously extracted gluten.

The invention also provides a kit that comprises the composition of the invention or the components of this composition partially mixed or separated. This kit can be used to extract the gluten contents of a heat-treated or non heat-treated food product, or to extract the gluten as a previous step to quantification by ELISA in order to determine the gluten contents of the food sample studied. The kit can also contain the other reagents required for the gluten extraction i.e. the aqueous solution of ethanol or its components separately, and/or the reagents required to perform ELISA to quantify the gluten contents of a food item, totally or partially mixed together or separately.

The following examples illustrate the invention and should not be considered to limit their application in any way.

EXAMPLE 1

Recovery of Gluten from Heat-Treated Food Products

This experiment was carried out to compare the efficacy of the procedure provided by this invention to extract gluten from heat-treated food items, at different temperatures, compared to the method usually used (Reference method).

1.1 Materials

The following food items were used for this example:

A) Food items treated at high temperatures during the manufacturing process (180-220° C.):

A.1) "Gluten-free" but contaminated with gluten (i.e. food products that claim not to contain gluten but that do in fact contain gluten); and, A.2) Food items that contain gluten; and A.3) "Gluten-free" food items not contaminated with gluten (i.e. foods that do not contain gluten for use as controls).

B) Foods treated at intermediate temperatures (approximately 110° C.); starches contaminated with gluten.

1.2 Reference Method

The reference method is the method currently used to extract gluten that uses a 60% solution of aqueous ethanol.

To apply this method, 0.125 g of the ground sample of food is weighed out and placed in a 10 ml propylene tube. Then, 5 ml of a 60% aqueous solution of ethanol is added and the reaction mixture is incubated for 1 hour, at room temperature, in a rotatory stirrer (LABINCO BV model (position 2-3)). After incubation, the samples are centrifuged for 10 min at 3,500 rpm (2,500 g), at room temperature (5810 Eppendorf centrifuge), and the supernatant is transferred to clean 10 ml propylene tubes and then analysed by an ELISA based on a single R5 monoclonal antibody, using for immunolocalisation and capture a horse-radish peroxidase (this ELISA is similar to the one described by L. Sorell et al., FEBS Letters, 439, 46-50 (1988) except that, in this case, the ELISA sandwich is based on a single monoclonal antibody using horseradish peroxidase for localisation and conjugate; this ELISA permits gluten from wheat, barley and rye to be quantified with a detection sensitivity of 1.5 ppm].

The 60% aqueous ethanol solution is prepared by mixing, for example in a test-tube, 300 ml of ethanol (Scharlau Nv 121) and 200 ml of milli-Q water (resistivity 18 MΩcm) and kept in a glass flask.

1.3 Process of the Invention

The process of the invention consists in extracting gluten using a 60% aqueous ethanol solution in the presence of a reducing agent and a dissociating agent and in the presence of a phosphate buffer of pH 7-8.

To carry out this process, 0.125 g of the ground food sample are introduced in a 10 ml propylene tube. After this, 1.25 ml of a composition (extraction cocktail) comprised of 250 mM 2-ME, 2 M guanidine hydrochloride and 0.1×PBS are added. The tubes are closed with screw/pressure stoppers and sealed with parafilm to prevent evaporation by heat. The reaction mixture is mixed in a vortex and incubated in an oven at 50° C. for 40 minutes. After the incubation, the reaction mixture is left to cool to room temperature and 3.75 ml of an aqueous solution of 80% ethanol are added to the reaction mixture that is incubated for 1 hour at room temperature in a rotatory stirrer (LABINCO BV model (position 2-3)). Then, the samples are centrifuged for 10 minutes at 3,500 rpm (2,500 g) at room temperature (Centrifuga 5810 Eppendorf) and the supernatant is transferred to clean 10 ml propylene tubes and then analysed by ELISA.

The 80% aqueous ethanol solution is prepared by mixing, for example in a test tube, 400 ml of ethanol (Scharlau Nv 121) and 100 ml of milli-Q water (resistivity 18 MΩcm) and kept in a glass flask.

The composition or extraction cocktail, comprised of 250 mM of 2-ME, 2 M hydrochloride and 0.1×PBS, is prepared, for example by weighing 3.8 g of guanidine hydrochloride Mr 95.53 (Fluka 50940) and by adding 15-18 ml of a solution of PBS (0.1×). Next, 349 μl of 14.29 M 2-ME are added (Sigma M-6250), this is made up to 20 ml with PBS (0.1×) and stirred until completely dissolved.

The 0.1×PBS solution can be prepared by diluting 1:100 of a 10×PBS solution. To do this, 1 ml of 10×PBS is added to a test-tube and made up to 100 ml with milli-Q water (resistivity 18 MΩcm). The resulting solution must have a pH between 7 and 8. The 10×PBS solution can be prepared by mixing and dissolving 80 g NaCl, 2 g KCl, 14.4 g $Na_2HPO_4$ in 900-950 ml of distilled water, in a 1l precipitation flask with a magnetic stirrer made up to the resulting solution with 1,000 ml of distilled water in a volumetric flask. The solution obtained is stored at room temperature.

1.4 Results

Table 1 shows the ELISA values of 23 food samples ("without gluten" but contaminated with gluten, food items containing gluten, and starches contaminated with gluten) that have been treated at high temperatures and 3 food controls "without gluten" not contaminated with gluten.

In this Table 1 it can be clearly observed in the 23 samples studied that an increased percentage of gluten is extracted with the process of the invention. This value increases by between approximately 30% and 173% in most food samples except for the 3 controls. The mean percentage of the increased value of gluten in these food products is 70.4%.

TABLE 1

Gluten analysis in heat-treated products extracted with 60% ethanol and with the extraction cocktail

| | Sample | 60% ethanol | Extraction cocktail | % Increase |
|---|---|---|---|---|
| 220° C. "Without gluten" contaminated | 4064 | 1.5 | 4.1 | 173.3 |
| | 4062 | 9.2 | 9.5 | 3.3 |
| | 4011 | 3.9 | 6.2 | 59.0 |
| | 1143 | 4.1 | 10.3 | 151.2 |
| | 3177 | 3.9 | 7.9 | 102.6 |
| | 3181 | 4.1 | 9.2 | 124.4 |
| 220° C. "Gluten" | 3569 | 13.9 | 25.5 | 83.5 |
| | 3576 | 8.4 | 21.3 | 153.6 |
| | 3577 | 15.4 | 20.7 | 34.4 |
| | 3578 | 3.1 | 4.2 | 35.5 |
| | 3579 | 7.6 | 7.9 | 3.9 |
| 110° C. "Starches" "Gluten" | 3619 | 8.6 | 11.2 | 30.2 |
| | 3624 | 14.5 | 18.8 | 29.7 |
| | 3683 | 3.6 | 7.9 | 119.4 |
| | 3817 | 7.8 | 14.0 | 79.5 |
| | 2162 | 4.0 | 6.9 | 72.5 |
| | 4146 | 2.0 | 3.7 | 85.0 |
| | 2159 | 6.5 | 9.4 | 44.6 |
| | 2160 | 5.0 | 6.9 | 38.0 |
| | 2161 | 3.0 | 4.1 | 36.7 |
| | 3592 | 8.2 | 14.2 | 73.2 |
| | 2195 | 6.3 | 10.2 | 61.9 |
| | 2163 | 4.3 | 5.8 | 34.9 |
| 220° C. "Without gluten" | 3515 | <0.15 | <0.15 | 00.0 |
| | 3428 | <0.15 | <0.15 | 00.0 |
| | 3511 | <0.15 | <0.15 | 00.0 |
| | | | | 70.4 |

Example 2

Quantitative Recovery of Gluten in Heat-Treated Food Products

This experiment illustrates the quantitative recovery of gluten, obtained by the process of the invention foods treated at different temperatures compared to the non-quantitative recovery of gluten obtained using the usual extraction method with 60% ethanol (Reference method).

2.1 Materials

To carry out this experiment the following were used:
1) breads made at different temperatures: 20° C., 60° C., 70° C., 90° C., 115° C., 150° C. and 220° C.; and
2) the flour used to make these breads 2.2 Reference Method The reference method used is that currently used to extract gluten using a 60% aqueous ethanol solution (see Example 1.2).

2.3 Process of the Invention

The process of the invention consists in extracting gluten using and aqueous ethanol solution of 60% in the presence of a reducing agent and a dissociating agent and in the presence of a buffer of pH 7-8 (see Example 1.3).

2.4 Results

The results obtained are shown in FIG. 1, which represents the percentage of gluten recovery in breads processed at different temperatures and in the flour with which these breads are made, and extracted by the reference method or by the process of the invention. The abscissa shows the temperatures at which the breads are processed and the ordinate represents the percentage gluten recovery taking the percentage recovery in the flours used to make the breads as 100%. FIG. 1 clearly shows the quantitative recovery of gluten in breads processed at different temperatures (almost 100% at any of the bread processing temperatures) when using the process of the invention compared to the non-quantitative recovery obtained using the reference method (60% ethanol). In this case, a continuous reduction of gluten recovery was observed (gluten recovery decreases proportionally as the temperature at which the bread is processed increases).

EXAMPLE 3

Gluten Recovery in Non Heat-Treated Foods

This experiment was carried out to compare the efficacy of the process of the invention to extract gluten from foods not treated with heat with that of the method usually used (Reference method).

3.1 Materials

To perform this experiment, 7 samples of wheat flour (Wh) were used and 1 of rye (R) that had not been submitted to any heat treatment (see Table 2).

3.2 Reference Method

The reference method is the method currently used to extract gluten using an aqueous ethanol solution of 60% (see Example 1.2).

3.3 Process of the Invention

The process of the invention consists in extracting gluten using an aqueous ethanol solution of 60% in the presence of a reducing agent and a dissociating agent and in the presence of a phosphate buffer of pH 7-8 [see Example 1.3].

3.4 Results

Table 2 shows the ELISA values of 8 food samples not treated with heat. This Table 2 clearly shows an increased percentage of gluten extracted with the process of the invention in the 8 samples studied. The increase in this value ranges from approximately 12% to approximately 47% in all foods studied including controls. The mean percentage of the increased gluten value in these foods is 27.3%.

TABLE 2

Gluten analysis in non heat-treated foods extracted with 60% ethanol and with the extraction cocktail.

| Sample | 60% ethanol | Extraction cocktail | % increase |
|---|---|---|---|
| Tr I | 5.6 | 8.2 | 46.4 |
| Tr II | 3.2 | 3.6 | 12.5 |
| Tr III | 5.6 | 8.1 | 44.6 |
| Tr IV | 5.2 | 6.1 | 17.3 |
| Tr V | 4.3 | 5.1 | 18.6 |
| Tr VI | 8.1 | 9.5 | 17.3 |
| Tr VII | 1.4 | 1.8 | 28.6 |
| Cn I | 7.3 | 9.7 | 32.9 |
|  |  |  | 27.3 |

The invention claimed is:

1. A process for extracting gluten from a food sample comprising extracting the gluten contents of said sample with an aqueous ethanol solution in the presence of a composition consisting of a disulphide group reducing agent and a dissociating agent in buffer with pH between 7 and 8, wherein the extraction process does not include contact between the food sample and any alcohol other than said ethanol.

2. The process of claim 1, wherein said aqueous ethanol solution has an ethanol content between 50 and 70%.

3. The process of claims 1, wherein said extraction comprises:
(a) mixing said sample with the composition consisting of a disulphide group reducing agent and a dissociating agent in a buffer with pH between 7 and 8 to make a mixture;
(b) incubating the mixture at a temperature of between 37 and 50° C., for a period of 30 to 60 minutes;
(c) cooling the mixture to room temperature;
(d) adding said aqueous ethanol solution; and
(e) separating the supernatant that contains the extracted gluten.

4. The process of claim 3, wherein said sample with the composition is incubated at a temperature of 50° C. for 40 minutes.

5. The process of claim 3, wherein said aqueous ethanol solution is an aqueous ethanol solution containing 60% of ethanol.

6. The process of claim 3 further comprising incubating the mixture after step (d).

7. The process of claim 6, wherein the incubation of the mixture after step (d) is done at room temperature for 1 hour.

8. A method to quantify by ELISA the amount of gluten present in a sample of food that comprises extracting said gluten from said sample using the process of claim 1 and quantifying by ELISA the gluten extracted.

9. A kit comprising a composition consisting of a disulphide group reducing agent and a disassociating agent in buffer with pH between 7 and 8 partially mixed or separate and an aqueous ethanol solution or separate components of the aqueous ethanol solution, wherein the kit does not include any alcohol except for said ethanol.

10. The kit of claim 9, further comprising ELISA reagents necessary to quantify gluten content of a food product, wherein said reagents are completely mixed, partially mixed or separate.

11. The process of claim 1, wherein the disulphide group reducing agent is selected from the group consisting of 2-mercaptoethanol, dithiotreitol and mixtures thereof.

12. The process of claim 1, wherein the disassociating agent is selected from the group consisting of guanidine hydrochloride, urea and mixtures thereof.

13. The process of claim 1 wherein the disulphide group reducing agent is 2-mercaptoethanol and the disassociating agent is guanidine hydrochloride.

14. The kit of claim 9, wherein the disulphide group reducing agent is selected from the group consisting of 2-mercaptoethanol, dithiotreitol and mixtures thereof.

15. The kit of claim 9, wherein the disassociating agent is selected from the group consisting of guanidine hydrochloride, urea and mixtures thereof.

16. The kit of claim 9 wherein the disulphide group reducing agent is 2-mercaptoethanol and the disassociating agent is guanidine hydrochloride.

17. The kit of claim 10, wherein the disulphide group reducing agent is selected from the group consisting of 2-mercaptoethanol, dithiotreitol and mixtures thereof.

18. The kit of claim 10, wherein the disassociating agent is selected from the group consisting of guanidine hydrochloride, urea and mixtures thereof.

19. The kit of claim 10 wherein the disulphide group reducing agent is 2-mercaptoethanol and the disassociating agent is guanidine hydrochloride.

* * * * *